(12) United States Patent
Wardlaw

(10) Patent No.: US 6,235,536 B1
(45) Date of Patent: *May 22, 2001

(54) ANALYSIS OF QUIESCENT ANTICOAGULATED WHOLE BLOOD SAMPLES

(75) Inventor: Stephen C. Wardlaw, Lyme, CT (US)

(73) Assignees: Robert A. Levine, Guilford, CT (US); Wardlaw Partners, LP, Lyme, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/249,721

(22) Filed: Feb. 12, 1999

Related U.S. Application Data

(60) Provisional application No. 60/077,206, filed on Mar. 7, 1998, provisional application No. 60/077,200, filed on Mar. 7, 1998, provisional application No. 60/077,201, filed on Mar. 7, 1998, and provisional application No. 60/077,199, filed on Mar. 7, 1998.

(51) Int. Cl.$^7$ .............................. A01N 1/00; G01N 21/76; G01N 33/48; G01N 21/00; G01C 11/12

(52) U.S. Cl. .................. 436/172; 435/2; 435/960; 436/56; 436/63; 436/64; 436/66; 436/70; 436/172; 436/165; 436/177; 436/800; 436/805; 436/807; 436/808; 436/809; 436/536; 436/538; 436/541; 436/533; 436/534; 422/50; 422/55; 422/58; 422/73; 422/68.1; 422/82.05; 356/244; 356/246

(58) Field of Search .................... 356/244, 246; 422/58, 50, 73, 55, 101, 68.1, 82.05; 436/536, 56, 538, 63, 541, 800, 533, 165, 534, 172, 805, 177, 807, 66, 808, 70, 809; 435/2, 960

(56) References Cited

U.S. PATENT DOCUMENTS 4,201,470 * 5/1980 Ehrly et al. ............................ 356/39

(List continued on next page.)

OTHER PUBLICATIONS

Miale, J., Laboratory Medicine, Hematology, fourth edition, pp. 592–594 and 643–646, (1972).*

Primary Examiner—Long V. Le
Assistant Examiner—Gailene R. Gabel
(74) Attorney, Agent, or Firm—William W. Jones

(57) ABSTRACT

Formed constituents of a quiescent anticoagulated whole blood sample are optically or visually analyzed in a sample chamber which has a varying through plane thickness due to convergent opposing sample chamber walls. At least one of the convergent walls of the chamber is transparent so that the blood sample constituents can be observed. The chamber's varying thickness produces a first lesser thickness region in the chamber wherein a quiescent monolayer of red blood cells in the sample will reside after the sample is introduced into and fills the chamber. Larger formed constituents such as white blood cells in the sample are unable to enter the aforesaid lesser thickness region of the chamber. The red cells which reside in the greater thickness regions will agglomerate to form rouleaux and lacunea. The exact thickness of the chamber at any particular location in the chamber can be predetermined, or can be determined in situ as the sample is being analyzed. By admixing certain dyes with the blood sample, various characteristics and other information can be derived from the various formed constituents in the sample by means of a scanning instrument which is able to measure various color and other signals emitted from the sample at various locations within the chamber, or by means of visual examination of the sample in the chamber. The thickness of the lacunae areas of the sample can be calculated by the instrument as a function of signal emission strength from the dyes or stains. The emissions can be the result of sample fluorescence or can be the result of signal density through the sample. Particle volumes can be measured as a function of signal emission suppression caused by the particles. Erythrocyte sedimentation rates (ESR) can also be derived from a blood sample disposed in the sampling chamber.

21 Claims, 4 Drawing Sheets

U.S. PATENT DOCUMENTS

| | | | |
|---|---|---|---|
| 4,400,370 | * 8/1983 | Kass | 424/3 |
| 4,790,640 | * 12/1988 | Nason | 350/534 |
| 4,882,284 | * 11/1989 | Kirchanski et al. | 436/63 |
| 5,427,959 | 6/1995 | Nishimura et al. | 436/534 |
| 5,723,285 | * 3/1998 | Levine et al. | 435/4 |
| 5,731,513 | * 3/1998 | Bull | 73/61.66 |

* cited by examiner

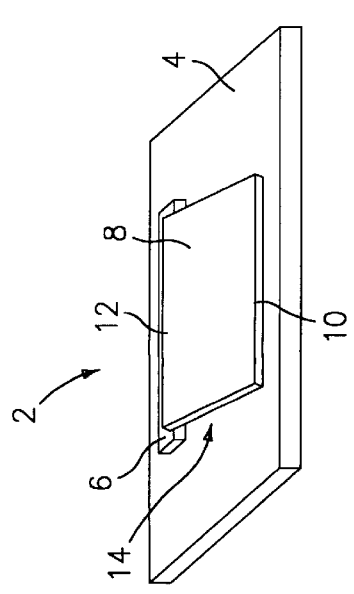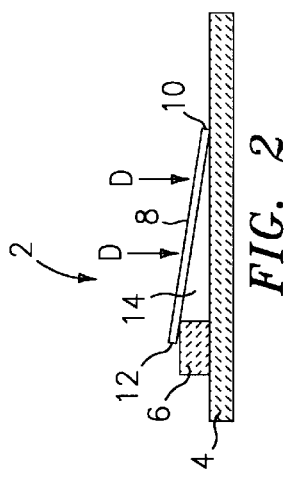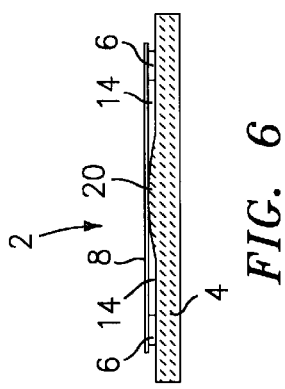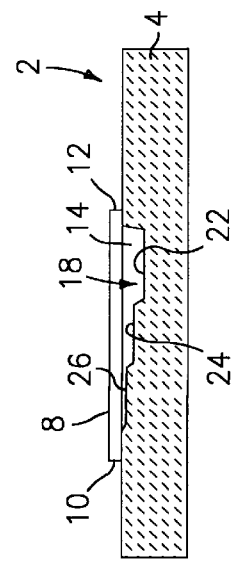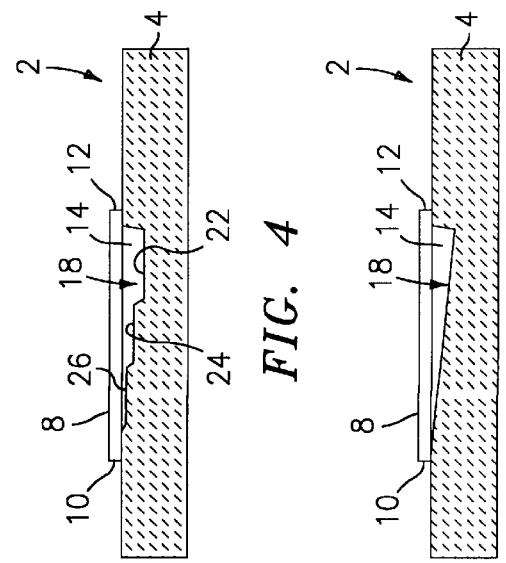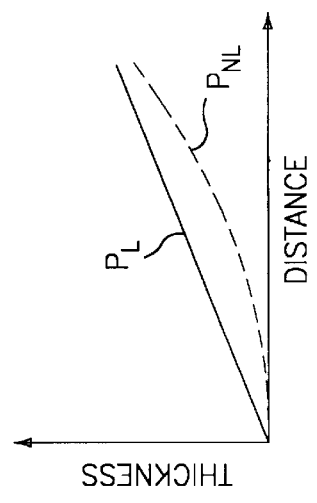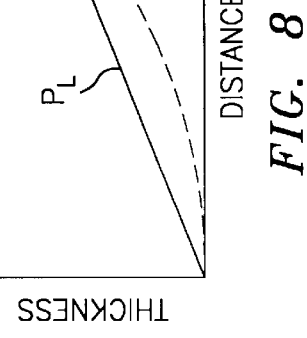

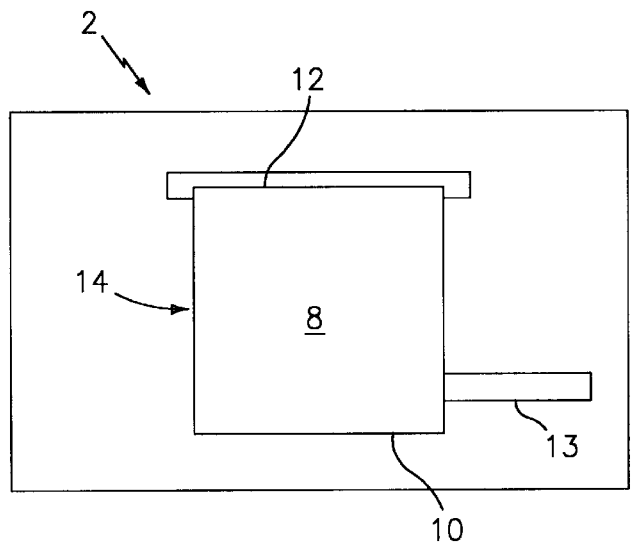
FIG. 7
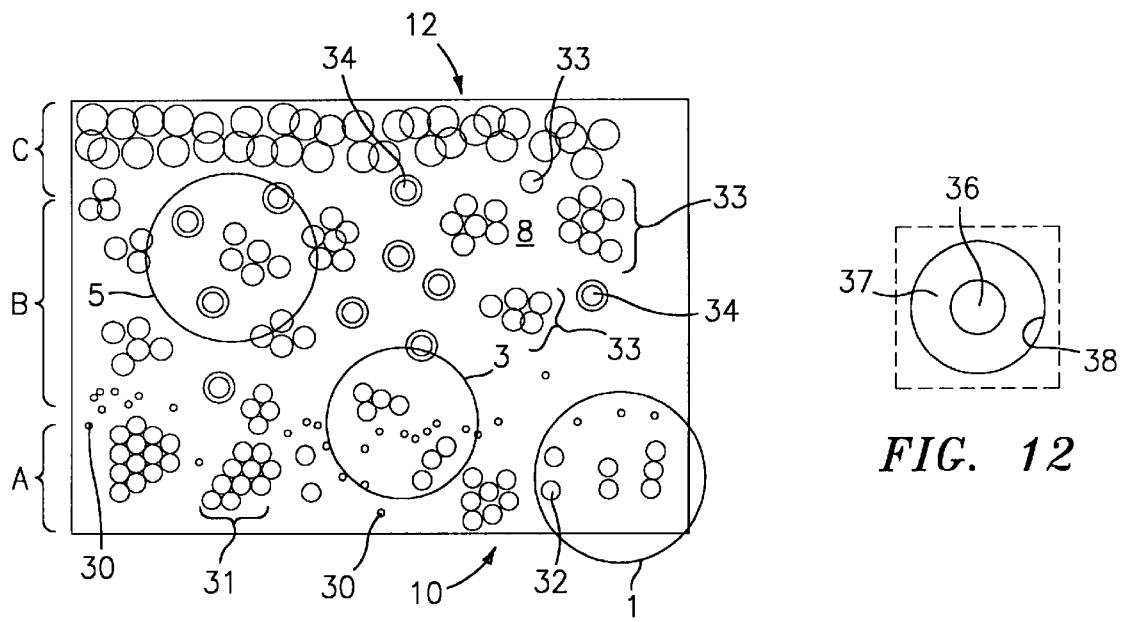
FIG. 9
FIG. 12
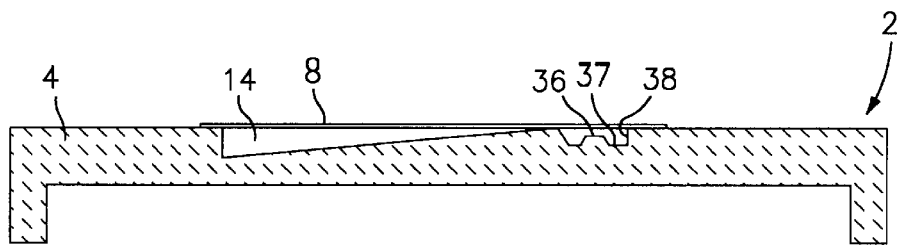
FIG. 11

ANALYSIS OF QUIESCENT ANTICOAGULATED WHOLE BLOOD SAMPLES

This application claims the benefit of the filing date of provisional patent applications Ser. Nos. 60/077,199 now abandoned; 60/077,200 now abandoned; 60/077,201 now abandoned; and 60/077,206 now abandoned; all filed on Mar. 7, 1996.

TECHNICAL FIELD

This invention relates to an apparatus and method for analyzing a quiescent sample of anticoagulated whole blood. More particularly, this invention relates to an apparatus and method for analyzing the blood sample in a quiescent state, without the need for fluid streams passing through the blood sample analysis apparatus during the analytic process. Blood constituent counts per unit volume of sample; blood constituent volumes; hematocrit; hemoglobin measurements; close approximation of erythrocyte sedimentation rates; and blood constituent type identification can all be performed using the apparatus and method of this invention.

BACKGROUND ART

Recent advances in biological fluid analysis, and in particular, analytical hematology have increased the quantity and quality of information available from a patients blood sample. As a result, the medical community's interest in using patients blood samples as a diagnostic tool has also increased, and the most commonly performed test performed on whole, anticoagulated blood is the complete blood count, or CBC, which is a suite of tests which are considered to include measurements of the hematocrit (Hct), hemoglobin (Hgb), red blood cell count (RBC). white blood cell count (WBC) and platelet count (Pit), red blood cell metrics such as the mean cell volume (MCV) and others, as well as the leukocyte differential count (LDC or "Diff") which is the classification of the types of white blood cells present. Compared to any other laboratory test, it is a peculiar characteristic of the CBC, that any instrument or method which performs it must do four different types of analyses. First, the general physical properties of the sample, namely the hematocrit and various cell or particle counts must be analyzed using quantitative methods relating to the entire sample. In conventional instrumentation and methods, this requires accurate sample metering and dilution, followed by specialized measurement apparatus. Secondly, a specific chemical property of the sample, namely the hemoglobin concentration, must be measured, usually by quantitative chemical means. Thirdly, the instrument must measure quantitative aspects of the individual cells, which usually involves providing a high dilution of the sample with a subsequent passage of the diluted material through a flow cell which measures the cells using electrical or optical means. Fourthly, qualitative measurements are used to classify the percentage of the total white blood cells which are composed of specific sub-populations. The number of sub-populations depends upon the sophistication of the instrument involved, which may be as little as two or more than seven classifications.

Historically, the different aspects of the CBC have been performed using separate methods. For example, the LDC portion of a CBC was traditionally performed by smearing a small amount of undiluted blood on a slide, staining the dried fixed film and examining the smear under a microscope. Reasonable results can be gained from such a smear, but the accuracy and reliability of the data depends largely on the technician's experience and technique. In addition, the use of blood smears is labor intensive and cost prohibitive, and is therefore generally not favored for commercial applications. Another method uses electrical impedance or optical flow cytometry. Flow cytometry involves passing a diluted blood sample through a small vessel wherein electrical impedance or optical sensors can evaluate the constituent cells as they pass serially through the vessel. The same apparatus may also be used to simultaneously enumerate and provide cell metric data. To evaluate WBC's and/or platelets, the blood sample must be diluted, and the sample must be treated to mitigate the overwhelming number of the RBC's relative to the WBC's and the platelets. Although more expedient and consistent than the above described smear methods, flow cytometry also possesses several disadvantages. One disadvantage of flow cytometry is the plumbing and fluid controls that are necessary for controlling the flow rate of the diluted blood sample past the sensors, The plumbing in current flow cytometers can, and often does, leak, thus potentially compromising the accuracy and the safety of the equipment. Another disadvantage of many current flow cytometers relates to the accuracy of the internal fluid flow controls and automated dilution equipment. The accuracy of the flow cytometer depends upon the accuracy of the fluid flow controls and the sample dilution equipment, and their ability to remain accurately calibrated. Flow controls and dilution equipment require periodic recalibration. The need for recalibration illustrates the potential for inaccurate results and the undesirable operating costs that exist with many presently available flow cytometers.

An article authored by John L. Haynes, and published in *Cytometry Supplement* 3:7–17 in 1988 describes the principles of flow cytometry, both impedance and optical, and the application of such a technology to various fields of endeavor. Blood samples being examined in flow cytometers are diluted anywhere from 10:1 to 50,000:1.

Erythrocyte sedimentation rate, which is an indicator of systemic inflammation, is another clinically significant test which is performed on anticoagulated whole blood. This test involves placing a sample of anticoagulated whole blood in a sample tube and allowing the erythrocytes to gravimetrically settle out in the tube over a period of one hour. The degree of erythrocyte settlement during the hour is reflective of systemic inflammation in the blood donor.

Another approach to cellular analysis is volumetric capillary scanning as outlined in U.S. Pat. Nos. 5,547,849; 5,585,246 and others, wherein a relatively undiluted sample of whole blood is placed into a capillary of known volume and thickness and is examined while the blood is in a quiescent state. This technique deals with the presence of the red blood cells by limiting the scanning wavelengths to those to which the red blood cells are relatively transparent, and it requires that the sample be treated so that the red blood cells do not aggregate during the measurement process. Thus, this technique is limited to the use of longer wavelength fluorescence, and there is no provision for the examination of red blood cells and platelets or the examination of any cellular morphology. Also, because the counts must occur in a constant volume, it is difficult or impossible to examine a wide range of sample particulate constituents in a single sample vessel, since the relative numbers of these constituents can vary over a thousand to one in a whole blood sample. There are a number of commercial instruments available for performing a CBC or related tests, but those which provide more than a few of the CBC tests quickly become complex, expensive and prone to malfunction. In addition, there are a number of methods proposed for specific hematological tests, but these do not provide all of the clinically useful information which is expected in a CBC.

Another problem with the more complex currently available instruments for performing CBC's is that they must be calibrated. This is because most of the dilutions and measurements are relative rather than absolute, so in order to provide exact quantitation, actual particulates, generally stabilized samples of whole blood with known values, must be analyzed by the instruments, and the instrument adjusted so that the correct values are produced. It should be obvious that this type of calibration is prone to errors in the preparation of the standard material and its stability during transportation and storage. The material is also expensive, which increases the cost of the tests. This calibration would not be required if all measurements were made on substantially undiluted samples using a method where any calibration was integral to the method.

Frederic L. Nason, in U.S. Pat. No. 4,790,640, describes the manufacture of a device wherein some cellular elements, namely sickle cells, can be separated from the mass of red blood cells by trapping them in a wedge-shaped chamber of decreasing, and preferably monocellular thickness. The aforesaid patent does not provide any suggestions as to how hematological information, such as cell counts, hematocrit, hemoglobin measurements, cell morphology examination, or how different formed constituents could be identified in the wedge-shaped chamber.

It would be desirable to have a method and apparatus for examining a quiescent sample of anticoagulated whole blood, which method and apparatus are capable of providing accurate qualitative and quantitative results on a number of different hematologic parameters, and does not require sample fluid flow through the sampling chamber during sample analysis.

DISCLOSURE OF THE INVENTION

This invention relates to a method and apparatus for use in examining and obtaining information from a quiescent substantially undiluted anticoagulated whole blood sample which is contained in a chamber. The phrase "substantially undiluted" as used in connection with this invention describes a blood sample which is diluted by no more than about 1:1, and preferably much less. Generally, the only reagents that will be used in performing the method of this invention are dyes, stains and anticoagulants, and these are not intended to dilute the sample. Preferably, the varying through plane thicknesses of the several regions in the chamber will create sufficient capillary forces in all regions of the chamber so as to cause spreading of the blood sample throughout the chamber which ultimately results in a quiescent blood sample in the chamber. The only motion in the blood sample will be Brownian motion of the blood sample's formed constituents, which motion is not disabling of the use of the device of this invention. The apparatus includes a sample-holding chamber which has opposite sample-containment walls, at least one of which is transparent, which walls converge in at least one portion of the chamber. The through plane thickness of the chamber thus varies in different regions of the chamber. As used in this disclosure, the phrase "through plane" refers to a line of sight which corresponds to the shortest distance between the convergent walls in any region of the chamber. The degree of convergence of the two walls, i.e., the distance between the two walls, at any particular point in the chamber is either known, or it can be measured after the sample has been placed in the chamber, as will be described hereinafter.

The thinnest region in the chamber will be sized so that a monolayer of individual red blood cells present in the sample will form when the chamber is filled with the blood sample. The thickness of this part of the chamber should be between about two and about seven microns, and is preferably about five microns. Thus measurements of the individual red cells, metrics such as the mean red cell volume (MCV) and mean corpuscular hemoglobin (MCH) can be measured in this area of the chamber, as will be described hereinafter.

From the thinnest portion of the chamber, the chamber thickness increases so as to form progressively thicker regions in the chamber that are used to identify and enumerate cellular or particulate elements in the blood sample. In all cases, such enumeration will occur in a region of the chamber where the thickness of the region can be determined, so that the cell or constituent counts can be given as a number of cells or constituents in a given volume of the sample. One of the thicker regions in the chamber will collect white blood cells and red cell rouleaux. The thickness of the chamber in this region thereof is typically in the range of between about seven to about forty microns.

The chamber is contained in a sample holder into which the blood sample can be drawn. Details of such a sample holder are disclosed in co-pending U.S. patent application U.S. Ser. No. 09/256,486, filed Feb. 23, 1999.

The sample to be assayed is admixed with a colorant which can be, for example, a fluorescent dye, and the resultant admixture spreads out in the chamber so as to form a quiescent sample that has a varying thickness due to the convergence of the walls of the chamber. The colorant can be added to the sample prior to admission of the sample into the chamber, or the colorant can be added to the sample while the sample is within the confines of the chamber, such as by dry coating the colorant on walls of the chamber. Anticoagulants can also be added to the blood sample before it is drawn into the chamber, or they can be admixed with the blood sample after the latter enters the chamber, such as by dry coating the anticoagulants on the walls of the chamber. Regions of interest in the chamber are individually illuminated by a light source having a selected wavelength, or wavelengths, which causes the colorant in the sample to fluoresce, or otherwise be quantitated. Regions in the chamber containing the various sized formed constituents in the blood sample are thus scanned, preferably by an optical instrument, and the results of the scans may be digitized and analyzed.

The sample will be manipulated or treated to ensure that there will be regions in the sample which do not contain formed constituents, and only contain the plasma portion of the blood sample in which cells or other formed constituents in the blood are suspended. The intensity per unit area of the emitted fluorescent or transmitted signal (optical density) in such formed constituent-free regions is directly related to the thickness of the plasma, therefore the degree of fluorescence or the optical density of the liquid increases as the thickness of the chamber increases. Likewise, the degree of fluorescence or optical density from the sample will diminish in proportion to the volume of any formed bodies in the blood sample which are operable to displace the colorant which is dissolved in the plasma.

The through plane distance between the chamber walls at any particular point in the chamber can be determined in several ways. When the angle of convergence of the two walls is fixed, then the thickness of the chamber at any particularly point is a function of the distance between the smallest chamber thickness region and the particular point being surveyed. When the angle of convergence of the two walls has been predetermined at the time of manufacture of the chamber, the device which contains the chamber can be bar coded or otherwise labeled so that the angle of convergence of the two walls can be determined by the instrument during use of the device, and the thickness of any particular region being surveyed can be determined as noted above.

Another way to measure the thickness of the chamber at any particular field being surveyed relates to the intensity of the fluorescence signal emanating from such particular fields, or from the optical density of an absorbing dye. In thin regions of the sample, the intensity of the fluorescence signal emanating from formed constituent-free clear areas in the sample is proportional to the thickness of the sample, and thus is also proportional to the thickness of those regions of the chamber. Thus the thickness of the sample in any particular region being surveyed can be measured by measuring the intensity of the colorant signal in such clear areas. The latter method for measuring the thickness of an area in the chamber being surveyed is aided by the inclusion of a known size calibration area in a cassette into which the chamber is incorporated, which calibration area is able to contact a portion of the colorant and sample. Once the calibration area is scanned and the colorant signal therefrom is measured, the scanning instrument will know that chamber thickness A emits colorant signal B, and also that fractions or multiples of B will equal proportional fractions or multiples of A. With this information the number of formed constituents per unit volume of sample can be counted since the area of any field of view of the scanning instrument will be known. By multiplying the known area of the field of view times the measured thickness of the field of view, the volume of the field of view can be calculated anywhere in the chamber where a clear area of the blood sample exists.

The chamber can also be used to measure the volume of formed constituents in the blood sample. This measurement is enabled by the scanning instrument knowing how much colorant signal alteration will result from a preformed geometric feature that is associated with the chamber, which feature has a predetermined volume. The feature can be a signal supressing volume that displaces the colored clear plasma; or the feature can be a signal enhancing volume that increases the colored clear plasma. In order to use the signal strength-to-volume relationship to measure the volume of formed constituents, the strength of fluorescent signal intensity, or optical density from the area of a formed constituent is integrated and is compared to the expected degree of fluorescent signal intensity or optical density in that location if no formed constituent were present. Because any decrement in the degree of signal intensity or optical density over the area of the formed constituent is due to the displacement of the colored plasma by the formed constituent, the volume of signal from this "missing colored plasma" is easily calculable, and is equal to the volume of the formed constituent. Thus, formed constituent volumes can be measured in the chamber. A variant of this technique has been published in an article by Martha L. Gray et al in *Cytometry:* Vol 3. #6, pages 428–434:1983. The technique of Gray et al was used in a flow cytometric system, and because the contained volume from which the cells excluded the colorant was indeterminate, calibration with cells of known volume was required. Because the volume of the field in this invention is known, no such calibration is required.

Other characteristics, such as constituent types, constituent morphology, and the like can also be determined by analyzing colorant signals emanating from the formed constituents. By using surface epitope-tagging labeled antibodies, further information regarding the formed constituents being studied in the blood sample can also be obtained by scanning the sample for such labeled antibodies, and determining whether such labeled antibodies are coupled with any formed constituents in the sample.

It is therefore an object of this invention to provide a method and apparatus for use in obtaining volumetrically related information from a quiescent anticoagulated whole blood sample.

It is an additional object of this invention to provide a method and apparatus of the characterized wherein said volumetrically related information can be obtained without the need to employ external standardization substances.

It is an additional object of this invention to provide a method and apparatus of the character described which allows a substantially undiluted whole blood sample to be examined for formed constituent enumeration-per-unit-sample-volume information.

It is a further object of this invention to provide a method and apparatus of the character described which includes a sample-containing chamber which has different through plane thickness regions that are formed by opposed convergent chamber walls, at least one of which walls is transparent so that the sample can be examined through the transparent wall either optically or visually.

It is another object of this invention to provide a method and apparatus of the character described wherein the various through plane thickness regions in the chamber are sized so as to enable determination of morphologic characteristics, counts, and volumes of different size individual cells and other formed components in the blood sample.

It is yet another object of this invention to provide a method and apparatus of the character described wherein an accurate estimate of an erythrocyte sedimentation rate can be derived from in the blood sample.

BRIEF DESCRIPTION OF THE DRAWINGS

These and other objects and advantages of the invention will become more readily apparent from the following detailed description of several embodiments of the invention when taken in conjunction with the accompanying drawings in which:

FIG. 1 is a schematic perspective view of a blood sample-analyzing device which includes a sample-receiving chamber, which chamber includes varying through plane thickness regions;

FIG. 2 is a cross-sectional view of a chamber of the type shown in FIG. 1 wherein the through plane thickness of the chamber varies in a linear fashion;

FIG. 3 is a cross-sectional view similar to FIG. 2, but showing a chamber wherein the through plane thickness of the chamber varies in a non-linear fashion;

FIG. 4 is a cross-sectional view of a different embodiment of a chamber having a varying through plane thickness, and wherein the through plane thickness of the chamber varies in a step-wise fashion;

FIG. 5 is a cross-sectional view similar to FIG. 4 but showing a chamber having a through plane thickness which varies in a linear fashion;

FIG. 6 is a cross-sectional view of yet another embodiment of a chamber having a varying through plane thickness;

FIG. 7 is a plan view of a sample chamber formed in accordance with this invention which includes a capillary tube for use in calibrating a scanning instrument which is used in analyzing the blood sample;

FIG. 8 is a plot of the relationship between chamber thickness and the distance from the smallest through plane thickness region in the chamber to any other through plane thickness region in the chamber, with the solid trace being representative of a linear chamber such as that shown in FIG. 2 and the broken trace being representative of a non-linear chamber such as that shown in FIG. 3;

FIG. 9 is a schematic plan view of a portion of a varying thickness chamber formed in accordance with this invention and illustrating in a schematic sense how the various size formed constituents in a quiescent fluid sample will separate into the various thickness regions in the chamber so as to be individually visible in different fields of view in the chamber;

FIG. 11 is a schematic side elevational view of an embodiment of a device employing the chamber of this invention which device also includes a colorant signal intensity calibration component;

FIG. 12 is a schematic plan view of the signal emission pattern emanating from the calibration component of FIG. 11.

DETAILED DESCRIPTION OF SPECIFIC EMBODIMENTS OF THE INVENTION

Figure 10:
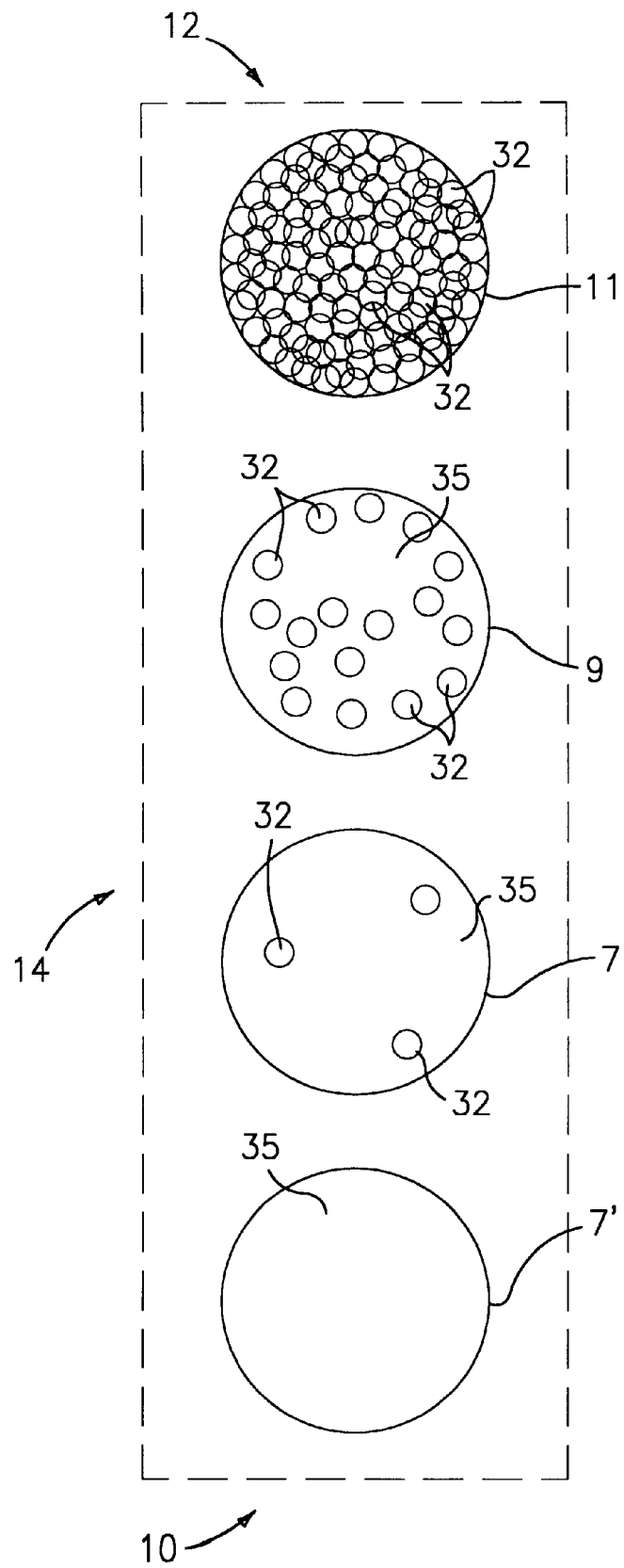
FIG. 10 is a schematic plan view of a portion of the chamber showing four different fields of view that might be surveyed by a sample-scanning instrument.

Referring now to the drawings, FIGS. 1 and 2 are schematic illustrations of a device which is denoted generally by the numeral 2, which device 2 includes a sample containing chamber 14 that has a varying through plane thickness. The device 2 includes a lower support wall 4, which for illustrative purposes may, for example, be a microscope slide. The device may also include a rectilinear shim 6; and an upper wall 8, which for illustrative purposes may be a microscope slide cover slip. At least one of the walls 4 and 8 is transparent so that the sample disposed therebetween can be examined through the transparent wall 4 or 8. If so desired, both of the walls 4 and 8 can be transparent. The wall 8 has one edge 10 which rests on, or very near, the wall 4, and an opposite edge 12 which is disposed on the upper surface of the shim 6. The result of the convergent relationship between the walls 4 and 8 is the formation of a chamber 14 that has a varying through plane thickness as measured in the through plane direction D, the through plane thickness increasing from the edge 10 to the opposite edge 12.

In the container assembly which is depicted in FIG. 2, the wall 8 is sufficiently rigid so as to produce a chamber 14 which varies in through plane thickness in a linear fashion from edge 10 to edge 12. In the container assembly 2 which is depicted in FIG. 3, the wall 8 is sufficiently flexible so as to produce a chamber 14 which varies in through plane thickness in a non-linear fashion from edge 10 to edge 12. The structures shown in FIGS. 2 and 3 will produce a chamber 14 which has an essentially infinite number of different through plane thickness regions into which formed constituents in the sample can reside after the sample has filled the chamber 14. Referring now to FIGS. 4 and 5, two further embodiments of the container assembly 2 are shown, both of which will also produce a sample chamber 14 having a varying through plane thickness. In the embodiments shown in both drawing figures, the device 2 includes a lower wall 4 and an upper wall 8. In the embodiments shown in both drawing figures, the lower wall 4 is formed with a generally tapered recessed surface 18 which converges toward the wall 8 in the direction starting at the edge 12 and commencing toward the edge 10 of the wall 8. In both embodiments of the device 2, the wall 8 is positioned flat on the upper surface of the wall 4. In the embodiment of the device 2 which is shown in FIG. 4, the recessed surface 18 includes a plurality of stepped increments 20, 22, 24, and more, if necessary, which are spaced apart from the wall 8 by predetermined distances. Thus, in the embodiment which is shown in FIG. 4, the surfaces of the chamber 14 converge from one edge of the chamber to an opposite edge of the chamber incrementally, rather than linearly or non-linearly. In the embodiment of the device 2 which is shown in FIG. 5, the recessed surface 18 converges at a constant angle toward the wall 8 whereby the through plane thickness of the chamber 14 varies linearly, as measured from the edge 12 to the edge 10 of the wall 8. The embodiments of the device 2 which are shown in FIGS. 4 and 5 thus illustrate a sample chamber 14 which includes regions of varying through plane thickness, which varies incrementally or linearly. It will be appreciated that by providing a convexly or concavely curved configuration to the recessed surface 18, a chamber with a non-linearly varying through plane thickness could be produced.

Referring now to FIG. 6, there is shown yet another embodiment of the device 2 which is operable to provide a variable thickness sample chamber 14. The device 2 includes a lower wall 4 and an upper wall 8, at least one of which is transparent. The lower wall 4 includes a medial protuberance 20, and the recessed surface 18 on the lower wall 4 surrounds the medial protuberance 20. In the specific embodiment illustrated in FIG. 6, the upper wall 8 is flat and its edges are elevated above the wall 4 and supported by shims 6. The surface 18 can be made curvilinear as shown in FIG. 6, or can be made rectilinear, as shown in FIG. 5. Thus, the chamber 14 formed in the embodiment of the device 2 shown in FIG. 6 can have a through plane thickness which varies in a linear fashion, or in a non-linear fashion. The surface 18 could also be formed with a stepwise declination, as shown in FIG. 4.

FIG. 8 is a graphic representation showing how the thickness of the chamber 14 varies from the thinnest edge 10 to the thickest edge 12. The solid line PL shows the thickness-distance relationship created by the chamber configurations shown in FIGS. 2 and 5; and the broken line PNL shows the thickness-distance relationship created by the chamber configurations shown in FIGS. 3 and 6. When the angle of convergence of the walls 4 and 8 is a known factor, this information can be pre-programmed into a computerized instrument which is used to scan the contents of the chamber 14.

FIG. 9 is a schematic representation of a plan view of the device 2 which incorporates the chamber 14, and of the manner in which any differently sized formed constituents present in the blood sample being examined will quiescently distribute in the chamber 14 when the latter is filled with the sample. The numeral 10 indicates a lesser thickness region of the chamber 14, and the numeral 12 indicates a greater thickness region of the chamber 14. In the representation of the device 2 shown in FIG. 9, there are three different thickness regions, A, B and C in the portion of the chamber 14 depicted. Region A is a lesser thickness region in the chamber 14; region B is a medium thickness region in the chamber 14; and region C is the largest thickness region in the chamber 14. Obviously, this particular number of different thickness regions is used merely to illustrate a primary feature of the chamber 14 of this invention, and is not limiting of the invention, since the chamber 14, as noted above, can include an essentially infinite number of different thickness regions. There are also three different fields of view 1, 3 and 5 shown in the FIG. 9. These fields of view 1, 3 and 5 are depicted as circles so as to illustrate the field of view as seen by an optical instrument, such as a microscope. In the illustration depicted in FIG. 9, the blood sample has filled the chamber 14 and has been quiescent for at least a few seconds. In the thinnest region A of the chamber 14 are found flattened red blood cells, either singly 32, or in monolayers 31. A few platelets 30 may also be found in the region A. Measurements of the mean red cell volume (MCV), mean corpuscular hemoglobin (MCH) and other cellular metrics may be made in the field of view 1, or in like fields of view found in the region A.

In the lower part of region B, there is sufficient room for the red blood cells to form rouleaux or other aggregates 33 which are surrounded by plasma that is free of the red blood cells. In field of view 3, the platelets 30 may be enumerated. In the upper part of region B, in field of view 5, there is sufficient chamber volume to allow the enumeration and classification of the white blood cells 34. The white blood cells 34 can thus be assayed in this region for surface receptor sites; can be typed; can be volumetrically measured; can be morphologically studied; and additional bits of information about the white blood cells 34 can be derived from the blood sample in the upper part of the region B. As the chamber thickness increases to that shown in region C, the red blood cell agglomerates 33 form a confluent layer, and the ability to locate white blood cells is reduced, although this region may be utilized for very low white cell counts.

FIG. 10 is a plan view of a fragment of the chamber 14, wherein the numeral 12 indicates a thicker end of the chamber 14 and the numeral 10 indicates a thinner and of the chamber 14. A chamber 14 having a varying thickness which varies from about zero to about three microns at its thinnest portion 10, to about two hundred microns at its thickest portion 12, will allow a one hundred fold dynamic range of particulate counts-per-unit-volume of blood sample. There are four schematic fields of view 7', 7, 9 and 11 shown in FIG. 9. Formed constituents 32 are depicted in each of the fields of view 7, 9 and 11, and none is shown in the field of view 7'. Open or clear fluid spaces 35 are also depicted in fields of view 7', 7 and 9, but not in field 11. This illustration demonstrates the dynamic useful range of the chamber 14 in finding fields of view which contain useful information. The constituents 32 shown in the drawing could be any of the aforesaid blood constituents, i.,e., platelets, red blood cells, or white blood cells. It will be noted that there are two fields of view, 11 and 7', which do not contain any useful information regarding the constituents 32, since the field of view 7' is devoid of constituents 32, and the field of view 11 is overly crowded with the constituents 32. However, the mere presence or absence of particulates may have meaning in certain circumstances, such as would be the case if abnormal cells were found. The fields of view 7 and 9 both contain constituents 32 and clear plasma areas 35. The scanning instrument may select one of these fields for detailed analysis. As noted above, as the scanning instrument searches the chamber 14 for useful regions in the chamber 14 in performance of an examination of the sample which involves deriving counts of the formed constituents 32 per unit volume of the sample in the chamber 14, it will see fields of view such as 7', 7, 9 and 11.

The scanning instrument can be programmed to ignore fields of view which do not have a clear fluid component 35 when performing a counting examination, since, in some cases, the presence of such a field component 35 is needed in order for the instrument to determine the depth of the field of view it is seeing, and also to ignore fields of view such as 7' which are devoid of formed constituents. As noted previously, the depth measurement may be a function of the colorant signal intensity emitted from the clear components 31 or a function of some other property, such as the X–Y position of the scanning instrument in the chamber. The scanning instrument contains a computer which is programmed to know the area of the field of view, and once the instrument determines the depth of any field of view, it can calculate the volume of that field of view. The scanning instrument may be programmed to ignore certain fields of view which have the necessary clear component 31 but do not also contain a significant number of formed constituents 32. Thus the scanning instrument might ignore the field of view 7, and will ignore the fields of view 7' and 11. In such a case, the scanning instrument might only count the number of formed constituents 32 in the field of view 9.

When the scanning instrument has surveyed a sufficient number of useful fields of view so as to have counted a clinically significant number of constituents 32, it will calculate the number of constituents 32 per unit volume of sample in the chamber 14. The determination of what constitutes a clinically significant number of counted constituents 32 will depend on predetermined clinically acceptable margins of error for the counting procedure. It will be appreciated that this number may vary depending on what constituents 32 are being counted. It will be understood that the scanning instrument computer will be programmed to know that it must move either toward the end 10 or the end 12 of the chamber 14 in order to find useful fields of view, depending on what is being seen in any particular field of view. Thus, when the instrument sees a field of view such as 11, it will know that it must move toward the end 10 of the chamber 14 in order to locate no more useful fields of view. Once a useful field of view such as 9 is located, the instrument will know that it will be likely to find similar fields of view in the chamber 14 by moving parallel to the edges 10 and 12 of the chamber 14. It should be noted that since some constituents will necessarily be excluded from some regions of the chamber 14, it follows that their concentration in the other regions will be increased. In practice, since the volume of sample in the thinnest regions of the chamber 14 is small in relation to the other examined volumes, its concentration effect is negligible. If the instrument has been programmed to look for fields of view which have ten or more constituents and also clear areas, so that it can perform a particulate count per field of view, it will select the field of view 9; it will identify the constituents 32 by their light emission characteristics; it will count the constituents 32 in the field 9; and it will establish the volume of the field 9, thus deriving a constituent count per the volume of the field 9. Specific constituent counts for the entire sample can be derived from seeking out and performing the same constituent counts in a clinically significant number of similar fields of view in the chamber 14.

White blood cells present in the sample which are supravitally stained with a colorant, such as acridine orange, may be identified by virtue of the cells' characteristic nuclear fluorescence at 540 nm and cytoplasmic fluorescence at 620 nm fluorescent emissions when excited by light in the 460 nm range. Nucleated red cells can also be identified following this procedure. The ratio of these two wavelengths can be used to identify any inflammatory cells, such as granulocytes. Other dyes such as astrozone orange may be used with similar wavelengths to perform a similar analysis. A more detailed description of this technique is contained in co-pending U.S. patent application U.S. Ser. No. 09/248,135, filed Feb. 10, 1999.

The hematocrit of the blood sample, which is typically defined in the U.S. as the percentage of a packed red cell column in a gravimetrically separated whole blood sample, but may be defined in Europe as a decimal or fraction of the packed red cell column in the whole blood sample, is measured by the scanning instrument in the following manner. A sensible marker, preferably a fluorescent dye having its emission wavelengths in the red, such as sulforhodamine S101, is intimately mixed with the blood sample. When the lacunae and red blood cell rouleaux form, the dye is caused to fluoresce in the sample, and a digital image of the lacunae and rouleaux areas of the sample is captured by the scanning instrument. This image is subjected to computer analysis wherein the first objective is to determine the average unit fluorescence of the plasma which makes up the lacunae. This may be done by digitally isolating the lacunae from the red blood cell rouleaux and averaging the signal intensity or brightness from the lacunae in the image. Another method is to generate a histogram of the intensity readings, where the highest readings represent those from the plasma. Since the lacunae contain essentially only plasma, their average signal intensity is equal to the average plasma signal intensity for the entire field of view being imaged. The scanning instrument then calculates the total signal intensity $B_t$ by multiplying the average signal intensity per pixel of plasma by the number of pixels in the field of view. The product of this step is what the total field of view signal intensity would be if there were no rouleaux in the field. The next step is to determine the actual signal intensity $B_a$ from the field of view being scanned. This determination is made by summing the actual signal intensity of all of the pixels contained in the field of view. The aforesaid image analyses may be performed by a number of commercially available software packages, such as those sold by the Signal Analytics Corporation of Vienna, Va., or other such image processing systems. If there were no red blood cells in the sample, that is, a hematocrit of zero, then the actual signal intensity $B_a$ would be equal to the calculated total signal intensity $B_t$. Since the red cells exclude the sensible marker, the presence of the red cells in the field of view diminishes $B_a$ in any particular field of view, and thus lowers $B_a$ as compared to $B_t$. Therefore, the hematocrit (Hct) of the field of view in the blood sample being scanned, expressed as a percentage of the total blood sample in the chamber, can be calculated as: Percent $Hct=[1-(B_a/B_t)]\times 100$. The Hct can also be expressed as a fraction of the total blood sample by solving the equation $Hct=1-(B_a/B_t)$. As noted above, a clinically significant number of fields of view should be scanned, and the hematocrit results from each scanned field of view should be averaged so as to obtain a reasonably precise hematocrit value for the entire blood sample.

While a fluorescent marker is preferred, a dye which absorbs transmitted light can also be used. When such a dye is used, the values of the optical signal density are measured rather than the fluorescent signal intensity, and $B_t$ is the average integral optical density per pixel of plasma multiplied by the imaged field of view's area, and Ba is the integral optical density over the area of the imaged field of view.

It should be understood that in order to measure the hematocrit, the sensible marker dye must not enter the red blood cells, or if it does enter the red blood cells, its contribution to the total signal must be capable of being calculated so that a correction can be made for the reduced effectiveness of the marker portion which has migrated into the red blood cells.

There are two general methods for determining the hemoglobin of the sample. The first involves determining the MCH of the sample by measuring the integrated optical densities of the red blood cells in field of view 1 shown in FIG. 9 in the Soret band at approximately 413 nm, or in the oxyhemoglobin band at about 550 nm. Since the absorbence of light at these wavelengths for hemoglobin is well known, the hemoglobin content of each red blood cell can be calculated, and an average value for the entire sample can be calculated after imaging a clinically significant number of red blood cells. This is the mean corpuscular hemoglobin (MCH). The MCH is proportional to the total sample hemoglobin divided by the red blood cell count (RBC), and therefore, the hemoglobin of the sample can be derived from the values of the MCH and the RBC. The determination of the RBC is described below. The MCV (expressed in femtoliters) is measured in field of view 1 shown in FIG. 9, where the red blood cells are present singly, or in a monolayer. The same dye and wavelengths that are used for the Hct are used for this determination. A digital image of the field of view is captured, and the signal from only the plasma is determined, as described above. Next, a single red blood cell is digitally isolated and the total fluorescence $S_1$ from the image is measured. Next, the number of pixels in the isolated red cell is multiplied by the average plasma signal $S_2$. The difference between the signals, $S_2 \cdot S_1$, represents the amount of signal excluded from the image due to the volume of the red blood cell. Using the signal/volume calibration factor described below, the volume of the single cell may be measured. The MCV may be calculated either by measuring the volumes of a number of single cells, or by determining the volume of a continuous group of cells and dividing by the number of cells within the group.

Mathematically, the MCV, expressed in femtoliters, is defined as the Hct, expressed as a percentage of the blood sample, divided by the RBC, expressed in units of one million cells per microliter of blood, thus the RBC can be calculated by solving the equation: $RBC=Hct\times 10MCV$.

FIGS. 7, 11 and 12 show a device 2 formed in accordance with this invention with various onboard structures which can be used to calibrate the instrument so that it can determine chamber field of view thicknesses after being calibrated during use by the reader instrument. Calibration of the device which allows the conversion of a colorant signal to a sample volume may be provided by any means which allows the measurement of colored plasma in a region where there is at least one volume-defined feature. In one instance, as shown in FIG. 7, a rectangular glass capillary 13 of known volume per unit length, and preferably of about 20 $\mu$ thickness is contiguous with one part of the chamber 14, whereby the capillary will fill with the sample and with the admixed colorant. After rouleaux forms within the capillary, the average plasma fluorescence can be determined by the methods described above. Since the volume-per-unit-length of the capillary is known since it is manufactured to a precise tolerance, the fluorescence per volume can be calculated by the scanning instrument.

Another calibration feature which may be incorporated into the device 2 is shown in FIGS. 11 and 12, and includes an in situ molded calibration-standard component 38 adjacent to and in fluid communication with the chamber 14. When the sample enters the chamber 14, the calibration standard component 38 will fill up with the stained or otherwise colored clear fluid component of the sample. The calibration component 38 may take the form of a well of accurately controlled depth which has a bottom floor 37, and a central protuberance 36 which extends upwardly from the floor 37 and which protuberance 36 has an accurately know volume. When the scanning instrument begins a counting procedure, it first goes to the component 38 and senses the signal intensity emanating from the floor 37 of the component 38. The average signal from the floor 37 will be used to calculate the total fluorescence which would be present if the protuberance 36 were not present. This is compared with the actual fluorescence signal from the area of the component 38 which includes the volume-displacing effect of the protuberance 36, and thus the difference between the calculated fluorescence and the actual fluorescence represents the the fluorescence displaced by the volume of the feature. That having been done, the scanning instrument will establish a known value of colorant signal decrement per unit volume in the chamber 14. The scanning instrument can then use this information to determine the volumes of the formed constituents in the sample. The scanning instrument will thus be provided with customized chamber region volumetric and formed constituent volumetric information for the particular colorant and device 2 that it is examining. The exact volumes and depths of the calibration devices used to calibrate the scanning instrument can be pre-programmed into the scanning instrument, or can contained in a bar code or other machine readable label placed on a cassette which contains the sampling chamber, and which label is read by the scanning instrument prior to the calibration step. The calibration component feature of the device of this invention is more thoroughly described in co-pending U.S. patent application U.S. Ser. No. 09/248,135, filed Feb. 10, 1999.

Figure 13:
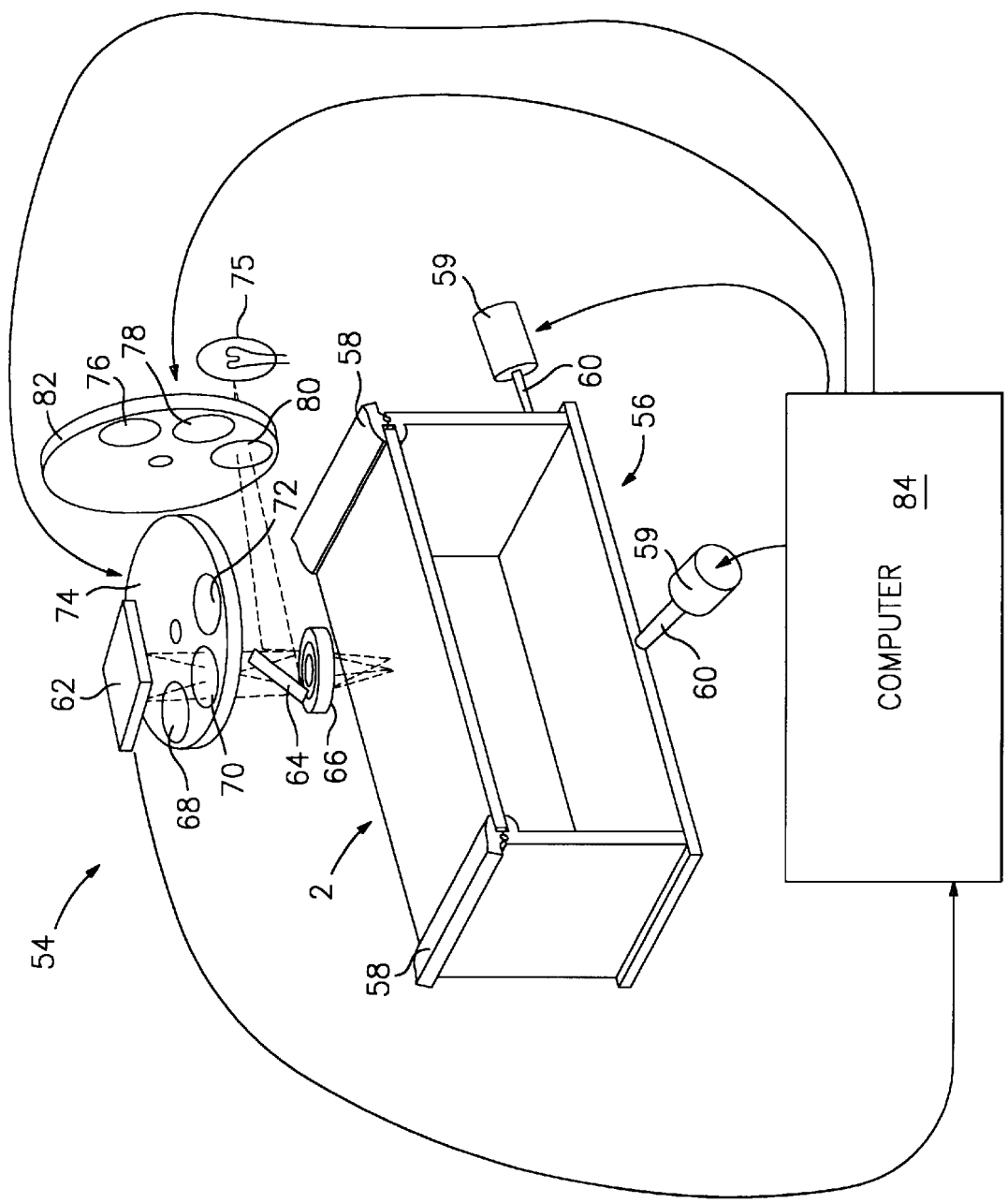
FIG. 13 is a schematic view of a scanning instrument which can be used to identify, count and analyze certain characteristics of the formed components of an anticoagulated whole blood sample placed in the chamber.

FIG. 13 is a schematic depiction of an automated colorimetric microscopical instrument assembly which is described in greater detail in co-pending U.S. patent application U.S. Ser. No. 09/255,673, filed Feb. 23, 1999. The instrument assembly is denoted generally by the numeral 54, and it can be used to scan a blood sample that is contained in the device 2, and can, without significant human intervention, calorimetrically analyze wavelengths of color emissions from various components of the blood sample thereby identifying the various components. It can also perform per-unit-blood sample volume counts of the various formed constituents in the sample; calorimetrically and/or morphometrically differentiate between different types of formed constituents in the blood sample being scanned; and can calorimetrically measure the hemoglobin content and the hematocrit of the blood sample. The instrument assembly 54 is designed to create and store or transmit the images of formed components in the blood sample being scanned. The instrument assembly 54 includes a stage 56 which includes clips 58 which engage the sample holder 2, and enables the sample holder 2 to be moved transversely in the X and Y directions as the contents of the sample holder 2 are scanned.

Reversible electric motors 59 can be used to selectively rotate drive screws 60 in opposite directions so that the sample holder 2 can be transversely moved in the X and Y directions. In this manner, the entire contents of the sample holder 2 can be scanned. The automatic embodiment of the instrument assembly 54 includes a CCD camera 62, a beam splitter 64, and lens 66 set which can be selectively moved in the Z direction so as to focus upon the sample-containing portions in the sample holder assembly 2. The CCD camera 62 views and records images of the sample through a plurality of different emission light wave filters 68, 70 and 72 which may be mounted on a selectively rotatable filter wheel 74. The instrument assembly 54 also includes an excitation light source 75 which directs an excitation light beam at the sample holder 2 through the beam splitter 64 and the focusing lens set 66. A series of excitation light wave length filters 76, 78 and 80 may be mounted on a selectively rotatable filter wheel 82. The excitation light beam is deflected by the beam splitter 64 toward the focusing lens 66, and is focused on the sample holder 2 by the lens 66. Thus, the two filter wheels 74 and 82 can allow one to selectively control and vary the wave lengths of the excitation light source, as well as the emitted light source. A pre-programmed processor controller 84 is operable to selectively control movement of the sample holder 2; the rotation of the filter wheels 74 and 82; and operation of the CCD camera 62. The controller 84 thus enables fully automatic operation of the instrument assembly 12 without the need of significant human intervention.

The equipment used in connection with this invention also enables the measurement of the erythrocyte sedimentation rate of a sample of blood placed in the sampling chamber. The erythrocyte sedimentation rate (ESR) is a measure of how far a column of red blood cells will fall in one hour when confined in a tube under specified conditions. The ESR is actually an indirect measure of how rapidly the red blood cells aggregate in a quiescent sample of anticoagulated whole blood. In samples where the red blood cells quickly aggregate, the red blood cells rapidly fall from suspension, thus resulting in a high ESR measurement, while in normal individuals, the red cells do not aggregate so rapidly, and thus remain in suspension longer and result in a lower ESR measurement. A more comprehensive description of the history and medical significance of the ESR is set forth in U.S. Pat. No. 5,506,145, Bull et al, granted Apr. 9, 1996, which is incorporated herein in its entirety.

In the present invention, the anticoagulated whole blood sample lies quiescently in a chamber, and the propensity of the red blood cells to aggregate and form rouleaux can be easily measured by examining the rapidity of red cell aggregate formation, and the size of the red cell aggregates. A preferred procedure for determining ESR using this invention involves scanning the region of the chamber where the red blood cell rouleaux and the plasma lacunae form in the quiescent blood sample. Multiple digital images of a field of view are taken beginning when the blood sample has been introduced in the chamber. The observed rate of red cell aggregation noted by the scans is a measure of the relative strength of the aggregation forces, and thus, a sample with a high ESR will also evidence a rapid formation of red cell aggregates, while a normal sample would show much slower rate of red cell aggregate formation. Additionally, red cell aggregates formed in the blood of patients with a higher ESR tend to be more compact and have fewer unattached cells than in samples from patients with a lower ESR. By measuring these parameters, a correlation between the rate and nature of red cell aggregate formation and the conventional ESR procedure can be established by standard correlation techniques.

Thus, by comparing a statistically significant number of conventionally performed ESR measurements of different blood samples with red cell aggregate formation parameters, as detected in accordance with this invention, from the same blood sample population will identify a correlation between the conventional ESR determination and the ESR determination method of this invention.

It will be noted that the method of this invention allows the measurement of several hematological parameters as a function of photometric emissions emanating from a quiescent sample of anticoagulated whole blood. The method of this invention enables the determination of ESR, Hct, Hgb, MCV, MCH and cell counts-per-unit-volume of the blood sample, all without the need of plumbing, the need to dilute the blood sample, and in a relatively small and compact sample container. The method of this invention also does not require that red blood cells be excluded from scanned fields of view, and indeed, the use of a substantially undiluted sample of anticoagulated whole blood practically guarantees that red cells, either individually, or in monolayers or in the form of rouleaux will be present in each useful field of view that is scanned by the instrument.

Since many changes and variations of the disclosed embodiments of the invention may be made without departing from the inventive concept, it is not intended to limit the invention otherwise than as required by the appended claims.

What is claimed is:

1. A method for measuring components of a complete blood count in a substantially undiluted quiescent sample of anticoagulated whole blood which is admixed with one or more colorants that are effective to differentially highlight various formed cellular constituents in the blood sample End also to color plasma in the blood sample, said blood sample and colorants being contained in a viewing container having varying thickness regions therein, said method comprising the steps of:
   a) scanning a plurality of fields of view of the blood sample with an optical instrument wherein each field of view having a known area;
   b) locating areas in said quiescent blood sample which areas contain plasma lacunae and either individual red blood cells, monolayers of red blood cells, or rouleaux of red blood cells, and other formed cellular constituents in the blood sample; and
   c) illuminating said areas in the quiescent blood sample with selected wavelengths of light so as to differentially highlight the various formed cellular constituents in the blood sample in a manner which will enable the derivation by said optical instrument of information regarding the concentration of such highlighted blood sample constituents per unit volume of blood in said sample.

2. The method of claim 1 wherein said scanning steps are performed in a first region of the content which contains rouleaux of red blood cells and plasma lacunae together in individual fields of view, and further comprising the step of calculating a hematocrit (Hct) value for the blood sample as a function of a calculated signal intensity or optical density which would emanate from a totally plasma-filled field of view, and a measured signal intensity or optical density emanating from an actual field of view in said first region.

3. The method of claim 2 wherein said first region has a thickness in the range of about seven microns to about forty microns.

4. The method of claim 2 wherein the step of calculating involves solving the equation: $Hct=1-(B_a/B_t)$, wherein $B_a$ is the measured signal intensity or optical density, and $B_t$ is the calculated total signal intensity or optical density.

5. The method of claim 2 wherein the step of calculating involves expressing the hematocrit as a percentage of the total blood sample and involves solving the equation: Percent $Hct=[1-(B_a/B_t]\times100$, wherein $B_a$ is the measured signal intensity or optical density, and $B_t$ is the calculated total signal intensity or optical density.

6. The method of claim 1 wherein said scanning steps are performed in regions of the container which contain individual red blood cells or a monolayer of red blood cells and plasma lacunae in individual fields of view; and further comprising the step of calculating a mean cell volume (MCV) for the red blood cells in the sample as a function of the difference between a measured signal intensity or optical density emanating from the plasma lacunae areas of the fields of view; and a measured signal intensity or optical density emanating from individual red blood cells or monolayers of red blood cells in the fields of view.

7. The method of claim 1 wherein said scanning steps are performed in a region of the container which contains both individual red blood cells or a monolayer of red blood cells and plasma lacunae in individual fields of view; and further comprising the step of calculating a red blood cell count (RBC) for the blood sample by solving the equation: RBC=Hct×10/MCV.

8. The method of claim 7 wherein "RBC" is expressed in units of millions of cells per microliter of sample, "Hct" is the calculated percent of the total sample which are red cells as derived from the blood sample, and "MCV" is the mean red blood cell volume value expressed in femtoliters which are derived from the blood sample.

9. The method of claim 7 comprising a further step of determining a hemoglobin value for the blood sample comprising the step of determining a mean corpuscular hemoglobin (MCH) by measuring integrated optical densities of red blood cells at 413 nm, or in an oxyhemoglobin band of about 550 nm.

10. The method of claim 9 comprising the further step of determining a (Hgb) value for the blood sample comprising the step of solving the equation: Hgb=MCH×RBC/10.

11. The method of claim 1 wherein said scanning steps are performed in a region of the container which also contains white blood cells, and further comprising the steps of: counting individual white blood cells in selected fields of view; and determining the volume of said selected fields of view so as to derive a white cell count per unit volume of blood sample.

12. The method of claim 11 wherein a number of different fields of view are scanned to derive said volumetric white cell count.

13. The method of claim 11 wherein said colorants are effective to differentiate types of white cells one from another by reason of different signal intensities emanating from various types of white cells, whereby a differential white cell count can be derived from said blood sample.

14. The method of claim 11 wherein the volumes of selected fields of view are determined by multiplying the area of the fields of view by the thickness of the container in each field of view.

15. The method of claim 14 wherein the thickness of the container in each field of view is calculated as a function of a measured signal intensity emanating from lacunae areas in each field of view.

16. The method of claim 14 wherein the thickness of the container in each field of view is determined as a function of the distance from a smallest thickness region in said chamber to the location of each field of view.

17. The method of claim 1 comprising the step of determining an erythrocyte sedimentation rate (ESR) correlation for a blood sample contained in said container, which ESR-correlation step includes measuring a rate of formation of red cell rouleaux in said container measuring a degree of compaction of the red cell rouleaux; and measuring an extent of red cells in rouleaux areas in the sample.

18. A method for measuring components of a complete blood count in a substantially undiluted quiescent sample of anticoagulated whole blood which is admixed with one or more colorants which are effective to differentially highlight various formed cellular constituents in the blood sample and also to color plasma in the blood sample, said blood sample and colorants being disposed in an at least partially transparent container having at least first and second regions which are in fluid communication with each other, said first region having a through plane thickness which is sized to contain either individual red blood cells or monolayers of red blood cells or rouleaux of red blood cells, and plasma lacunae; and said second region having a through plane thickness which is sized to contain white blood cells, said method comprising the steps of:
- a) scanning a plurality of fields of view in said first region with an optical instrument having a known area for each field of view while illuminating said first region with selected wavelengths of light;
- b) calculating various red blood cell parameters as a function of calculated and measured signal intensities emanating from said plurality of fields of view in said first region;
- c) scanning said second region with said optical instrument while illuminating said second region with said selected wavelengths of light; and
- d) counting individual white cells in selected fields of view in said second region and determining the volume of said selected fields of view so as to derive a volumetric white cell count per unit volume of the blood sample.

19. A method for measuring components of a complete blood count in a substantially undiluted quiescent sample of anticoagulated whole blood which is admixed with one or more colorants which are effective to differentially highlight various formed cellular constituents in the blood sample and also to color plasma in the blood sample, said blood sample and colorants being disposed in an at least partially transparent container having at least first and second regions which are in fluid communication with each other, said first region having a through plane thickness which is sized to contain either individual red blood cells or monolayers of red blood cells or rouleaux of red blood cells, and plasma lacunae; and said second region, having a through plane thickness which is sized to contain white blood cells, said method comprising the steps of:
- a) scanning a plurality of fields of new in said first region with an optical instrument having a known area for each field of view while illuminating said first region with selected wavelengths of light; and
- b) calculating various red blood cell parameters as a function of calculated and measured signal intensities emanating from said plurality fields of view in said first region.

20. A method for measuring components of a complete blood count in a substantially undiluted quiescent sample of anticoagulated whole blood which is admixed with one or more colorants which are effective to differentially highlight various formed cellular constituents in the blood sample and also to color plasma in the blood sample, said blood sample and colorants being disposed in an at least partially transparent container having at least first and second regions which are in fluid communication with each other, said first region having a through plane thickness which is sized to contain either individual red blood cells or monolayers of red blood cells or rouleaux of red blood cells, and plasma lacunae; said second region having a through plane thickness which is sized to contain white blood cells, said method comprising the steps of:
- a) scanning a plurality of fields of view in said first region with an optical instrument having a known area for each field of view while illuminating said first region with selected wavelengths of light; and
- b) scanning said second region with said optical instrument while illuminating said second region with said selected wavelengths of light; and
- c) counting individual white cells in selected fields of view in said second region and determining the volume of said selected fields of view so as to derive a white cell count per unit volume of the blood sample.

21. A method for measuring components of a complete blood count in a substantially undiluted quiescent sample of anticoagulated whole blood which is admixed with one or more colorants which are effective to differentially highlight various formed cellular constituents in the blood sample and also to color plasma in the blood sample, said blood sample and colorants being disposed in an at least partially transparent container having at least first and second regions which are in fluid communication with each other, said first region having a through plane thickness which is sized to contain either individual red blood cells or monolayers of red blood cells or rouleaux of red blood cells, and plasma lacunae; and said second region having a through plane thickness which is sized to contain white blood cells, said method comprising the steps of:
- a) scanning selected fields of view in said first region with an optical instrument having a known area for each field of view, while illuminating said first region with selected wavelengths of light, so as to differentially highlight various cellular formed constituents in the blood sample which are located in said fields of view; and
- b) deriving information regarding the differentially highlighted formed constituents which are located in said selected fields of view in said first region.

* * * * *

UNITED STATES PATENT AND TRADEMARK OFFICE
CERTIFICATE OF CORRECTION

PATENT NO. : 6,235,536 B1  Page 1 of 1
DATED : May 22, 2001
INVENTOR(S) : Stephen C. Wardlaw It is certified that error appears in the above-identified patent and that said Letters Patent is hereby corrected as shown below:

Column 1,
Line 5 of the specification, "1996" should be -- 1998 --; and

Column 15,
Line 26, "End" should be -- and --.

Signed and Sealed this

Twenty-seventh Day of November, 2001

*Attest:*

*Attesting Officer*

NICHOLAS P. GODICI
*Acting Director of the United States Patent and Trademark Office*